United States Patent
Liu

(10) Patent No.: US 10,520,424 B2
(45) Date of Patent: Dec. 31, 2019

(54) ADAPTIVE METHOD FOR A LIGHT SOURCE FOR INSPECTING AN ARTICLE

(71) Applicant: Hiwin Technologies Corp., Taichung (TW)

(72) Inventor: Ming-Shiou Liu, Taichung (TW)

(73) Assignee: HIWIN TECHNOLOGIES CORP., Taichung (TW)

( * ) Notice: Subject to any disclaimer, the term of this patent is extended or adjusted under 35 U.S.C. 154(b) by 64 days.

(21) Appl. No.: 15/943,808

(22) Filed: Apr. 3, 2018

(65) Prior Publication Data

US 2019/0302004 A1    Oct. 3, 2019

(51) Int. Cl.
| | |
|---|---|
| H04N 7/18 | (2006.01) |
| G01N 21/88 | (2006.01) |
| G01N 21/958 | (2006.01) |
| G01N 21/01 | (2006.01) |
| H04N 5/225 | (2006.01) |
| G03B 21/20 | (2006.01) |

(52) U.S. Cl.
CPC ......... G01N 21/01 (2013.01); G03B 21/2006 (2013.01); H04N 5/2256 (2013.01)

(58) Field of Classification Search
CPC .... G02B 13/004; G02B 13/006; G02B 13/04; G02B 13/146; G02B 13/18; G02B 27/0025; G02B 5/005; G02B 5/208; G02B 9/34; H04N 5/33; G01B 11/24; G01N 21/8851
See application file for complete search history.

(56) References Cited

U.S. PATENT DOCUMENTS

| | | | | |
|---|---|---|---|---|
| 6,207,946 | B1 * | 3/2001 | Jusoh | G01N 21/8806 250/208.1 |
| 6,627,863 | B2 * | 9/2003 | Wasserman | G01J 1/32 250/205 |
| 6,987,876 | B2 * | 1/2006 | Silber | G01J 1/32 250/205 |
| 7,986,856 | B2 * | 7/2011 | Chiang | H04N 5/243 358/521 |
| 2009/0317018 | A1 | 12/2009 | Chang et al. | |
| 2015/0235597 | A1 * | 8/2015 | Meng | G02F 1/1336 345/102 |
| 2017/0124689 | A1 * | 5/2017 | Doba | G03B 15/02 |
| 2017/0186148 | A1 * | 6/2017 | Uemura | G06T 7/0004 |

FOREIGN PATENT DOCUMENTS

| | | |
|---|---|---|
| JP | 2006-047389 A | 2/2006 |
| JP | 2016-033787 A | 3/2016 |

OTHER PUBLICATIONS

Office Action issued in corresponding Japanese application No. 2018-118712 dated Jul. 29, 2019.

* cited by examiner

*Primary Examiner* — Jessica M Prince
(74) *Attorney, Agent, or Firm* — Birch, Stewart, Kolasch & Birch, LLP

(57) ABSTRACT

A method includes selecting a candidate image property data set and a corresponding candidate light source parameter set, obtaining multiple adjusted light source parameter sets based on the candidate light source parameter set, projecting light onto an article and capturing images in multiple projecting modes, one by one, according to the adjusted light source parameter sets, obtaining multiple adjusted image property data sets each from the images captured in one projecting mode, and selecting a target image property data set from the adjusted image property data sets and a corresponding target light source parameter set.

16 Claims, 9 Drawing Sheets

ADAPTIVE METHOD FOR A LIGHT SOURCE FOR INSPECTING AN ARTICLE

FIELD

The disclosure relates to an adaptive method for a light source, and more particularly to an adaptive method for a light source that is used for inspecting an article.

BACKGROUND

U.S. Pat. No. 6,207,946 provides an adaptive lighting system for use with a machine vision apparatus for capturing high contrast images of an article to be inspected. The adaptive lighting system includes an array of plural optical fiber light emitting elements for projecting light onto an article to be inspected, a camera for recording an image of the article, a light intensity control circuit for varying intensity of the light emitted by the array to adjust the illumination of the article viewed by the camera, and a processor programmed to calculate a median gray value from a predetermined number of camera pixel intensity values of the article to re-adjust the intensity of the light until a setting with suitable contrast is reached.

However, the adaptive lighting system can only adjust the intensity of the light emitted by the array of plural optical fiber light emitting elements according to the contrast of the image, and, in practice, it is insufficient to consider the contrast alone. Moreover, besides the intensity of the light, other factors such as pattern, tone, etc., of the light impinging on the article are also important, and may affect the contrast and other image properties of the image of the article illuminated by the light.

SUMMARY

Therefore, an object of the disclosure is to provide an adaptive method for a light source that is used for inspecting an article. The adaptive method is to be implemented using an automatic adapting system that includes a storage device, a light source, an image capturing device and a processing unit. The light source is configured to project light onto the article in a plurality of initial projecting modes. The storage device stores a plurality of initial light source parameter sets corresponding respectively to the initial projecting modes, and a plurality of initial image property data sets. Each of the initial image property data sets is obtained by illuminating the article in a respective one of the initial projecting modes, and includes a plurality of property value sets that are related respectively to a plurality of image properties.

The adaptive method includes steps of:
selecting, by the processing unit, a candidate image property data set from the initial image property data sets according to a screening condition, the screening condition being related to the article and to at least one of the image properties;
selecting, by the processing unit, a candidate light source parameter set that corresponds to the candidate image property data set from the initial light source parameter sets;
obtaining, by the processing unit, a plurality of adjusted light source parameter sets based on the candidate light source parameter set;
controlling, by the processing unit, the light source to project light onto the article in a plurality of adjusted projecting modes according to the adjusted light source parameter sets, respectively;
capturing, by the image capturing device, a plurality of adjusted images of the article when the article is lighted up by the light source in each of the adjusted projecting modes;
obtaining, by the processing unit, a plurality of adjusted image property data sets each being obtained from the adjusted images that are captured in a respective one of the adjusted projecting modes, and each including a plurality of property value sets that are related respectively to the image properties;
selecting, by the processing unit, a target image property data set from the adjusted image property data sets according to the screening condition; and selecting, by the processing unit, a target light source parameter set that corresponds to the target image property data set from the adjusted light source parameter sets.

BRIEF DESCRIPTION OF THE DRAWINGS

Other features and advantages of the disclosure will become apparent in the following detailed description of the embodiment (s) with reference to the accompanying drawings, of which.

DETAILED DESCRIPTION

Figure 1:
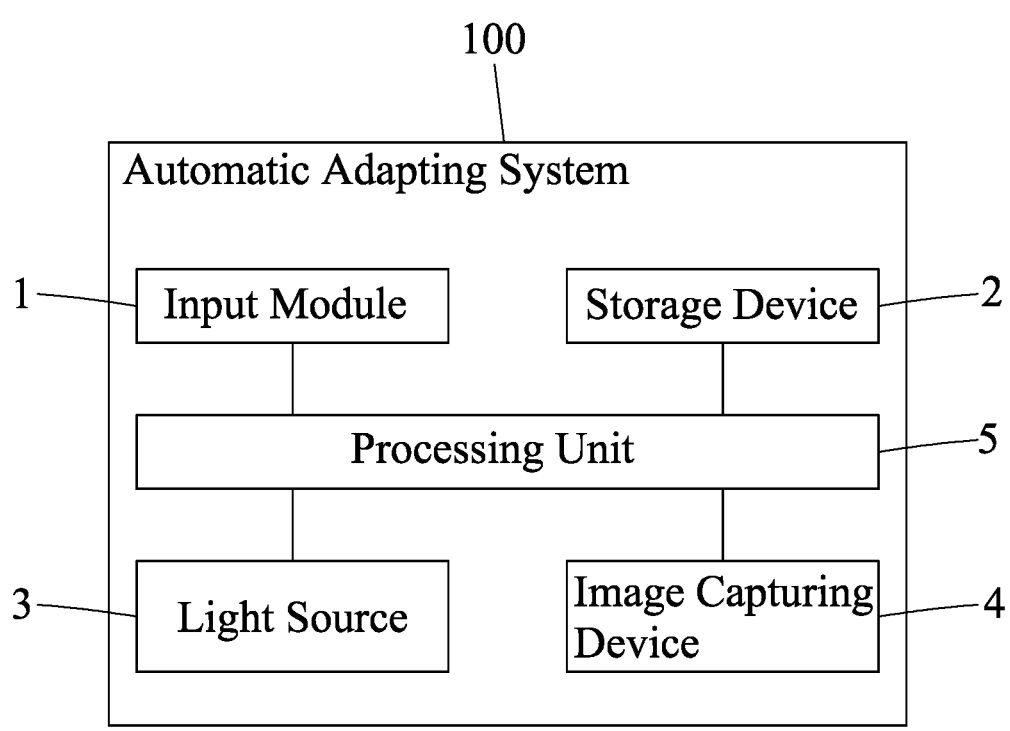
FIG. 1 is a block diagram illustrating an automatic adapting system for implementing an adaptive method for a light source that is used for inspecting an article according to one embodiment of this disclosure.

Referring to FIG. 1, an automatic adapting system 100 is configured to implement an adaptive method for a light source that is used for inspecting an article according to one embodiment of this disclosure. The automatic adapting system 100 includes an input module 1, a storage device 2, a light source 3, an image capturing device 4 and a processing unit 5. The processing unit 5 is electrically connected to the storage device 2, the light source 3 and the image capturing device 4, and is programmed to control the light source 3 to project light onto an article to be inspected in a plurality of initial projecting modes.

The light source 2 is, for example, an array of light emitting elements, such as light-emitting diodes. The image capturing device 4 is, for example, a camera for capturing an image of the article.

The storage device 2 may include any non-transitory memory mechanism for storing data in a form readable by a machine (e.g., a computer). For example, examples of a computer-readable storage device may include read-only memory (ROM), random-access memory (RAM), magnetic disk storage media, optical storage media, flash memory devices, and other storage devices and media. The storage device 2 is to store a plurality of initial light source parameter sets corresponding respectively to the initial projecting modes, and a plurality of initial image property data sets. Each of the initial light source parameter sets includes an initial brightness value and an initial tonal value, according to which the processing unit 5 controls the light source 3 to project light in the corresponding one of the initial projecting modes. Each of the initial image property data sets is obtained by illuminating the article in a respective one of the initial projecting modes.

The term "processing unit" may refer to any device or portion of a device that processes electronic data from registers and/or memory to trans form the electronic data into other electronic data. For example, the processing unit 5 is, but not limited to, a single-core processor, a multi-core processor, a dual-core mobile processor, a microprocessor, a microcontroller, a digital signal processor (DSP), a field-programmable gate array (FPGA), an application specific integrated circuit (ASIC), a radio-frequency integrated circuit (RFIC), etc.

The adaptive method for a light source that is used for inspecting an article includes a candidate selection procedure, a target selection procedure and an optimization procedure according to some embodiments of this disclosure.

Figure 2:
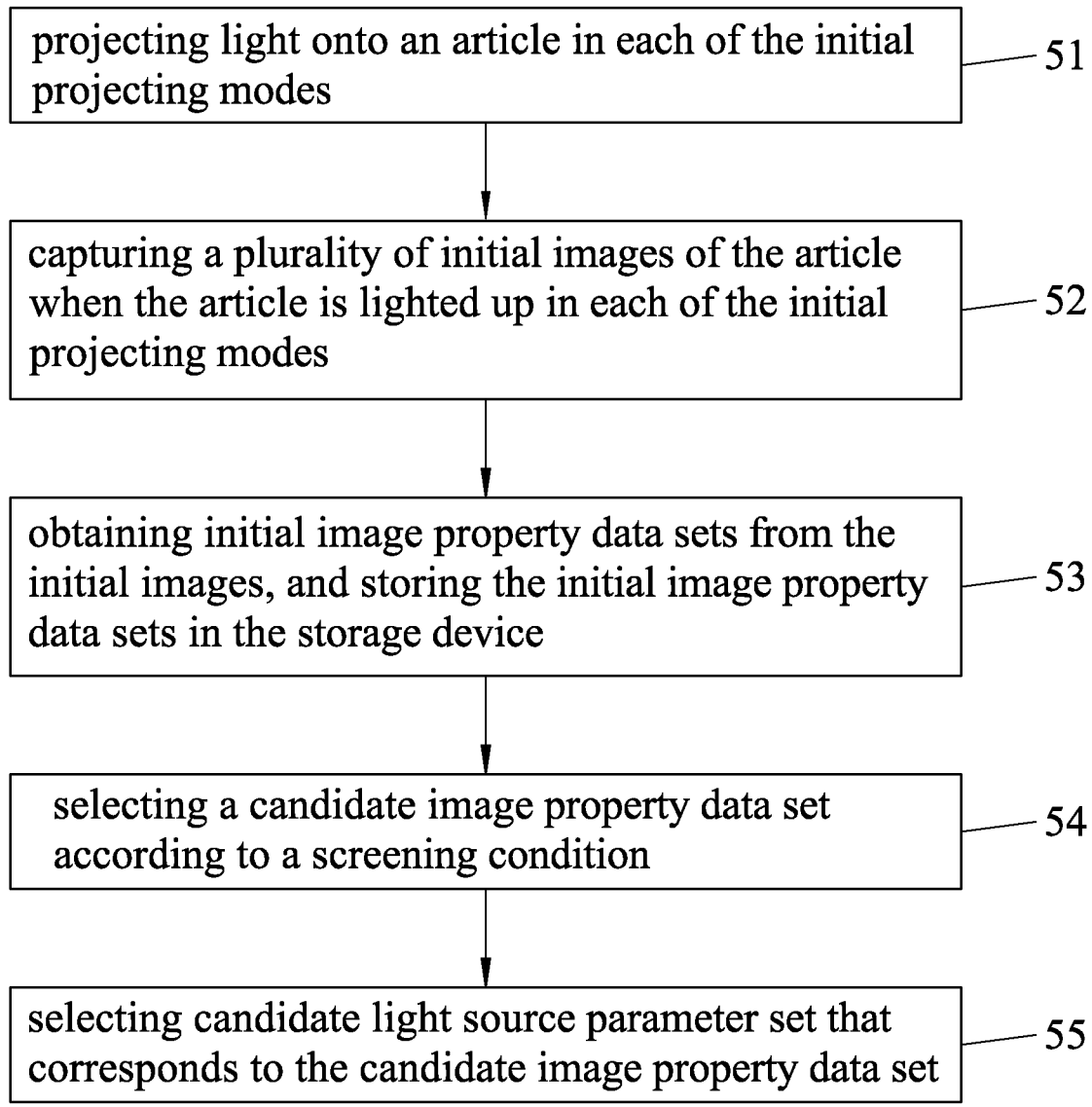
FIG. 2 is a flowchart of a candidate selection procedure of the adaptive method according to one embodiment of this disclosure.

Referring to FIG. 2, the candidate selection procedure is to select a candidate light source parameter set from the initial light source parameter sets (i.e., selecting a candidate projecting mode from the initial projecting modes), and includes the following steps 51 to 55.

In step 51, the processing unit 5 controls the light source 3 to project light onto the article in the initial projecting modes one by one, according to the corresponding one of the initial light source parameter sets.

In step 52, the image capturing device 4 captures a plurality of initial images of the article when the article is lighted up by the light source 3 in each of the initial projecting modes. In the description hereinafter, a set of the initial images that are captured in one of the initial projecting modes may be referred to as "relevant images."

In step 53, the processing unit 5 analyzes the initial images to obtain the initial image property data sets, and stores the initial image property data sets in the storage device 2. In particular, each of the initial image property data sets is obtained from the initial images that are captured in the respective one of the initial projecting modes. Each of the initial image property data sets includes a plurality of property value sets that are related respectively to a plurality of image properties, and each of the property value sets includes a first property value and a second property value that are related to one of the image properties corresponding to the initial image property data set.

For example, the image properties of an image may include image contrast, image stability, repeatability of image orientation, absolute accuracy of image orientation, repeatability of measurement of image size, density of data points of a point cloud, repeatability of data points of a three-dimensional (3D) point cloud, an error of the image from actual data (e.g., a CAD file of the article), etc. The following description is provided for explaining how to obtain, for each of the initial projecting modes, the first property value and the second property value of each of the property value sets included in the respective one of the initial image property data sets. In some embodiments, the first property value is, but not limited to, an average value.

In some embodiments, the second property value is, but not limited to, a standard deviation value.

For the property value set related to image contrast, the first property value is an average value of contrast ratios respectively of the relevant images, and the second property value is a standard deviation value of the contrast ratios.

For the property value set related to image stability, the first property value is a first default value predetermined by the processing unit 5, and the second property value is a standard deviation value of the relevant images. For example, the processing unit 5 calculates, for each of the relevant images, an average value or a total value of pixel values thereof, and then, calculates a standard deviation value of the average values or the total values respectively of the relevant images to serve as the standard deviation value of the relevant images. In some embodiments, the processing unit 5 calculates, for each of the relevant images, a standard deviation value of the pixel values thereof, and then calculates an average value of the standard deviation values to serve as the standard deviation value of the relevant images.

For the property value set related to repeatability of image orientation, the first property value is a second default value predetermined by the processing unit 5, and the second property value is obtained according to positions of the same feature point respectively in the relevant images. In some embodiments, the processing unit 5 calculates a standard deviation value of the positions of the same feature point respectively in the relevant images to serve as the second property value of the property value set related to repeatability of image orientation.

The property value set related to absolute accuracy of image orientation is obtained according to a first relative distance of a first pair of feature points in each of the relevant images and an actual distance between the first pair of feature points. In some embodiments, the processing unit 5 calculates a difference value between the first relative distance and the actual distance for each of the relevant images, and then calculates an average value of the difference values, which are calculated respectively for the relevant images, to serve as the first property value of the property value set related to absolute accuracy of image orientation. In some embodiments, the processing unit 5 calculates a standard deviation value of the difference values for the relevant images to serve as the second property value of the property value set related to absolute accuracy of image orientation.

The property value set related to repeatability of the measurement of image size is obtained according to a second relative distance between a second pair of feature points in each of the relevant images, and in particular, the physical meaning of the second relative distance between the second pair of feature points is a length of one edge of the article in the image. In some embodiments, the first property value of the property value set related to repeatability of measurement of image size is a third default value predetermined by the processing unit 5. In some embodiments, the processing unit 5 calculates a standard deviation value of the second relative distances for the relevant images to serve as the second property value of the property value set related to repeatability of measurement of image size.

For the property value set related to density of data points of a point cloud, the processing unit 5 first obtains, for each of the relevant images, a density value related to the distribution of the data points, and then calculates an average value of the density values respectively of the relevant images to serve as the first property value, and calculates a standard deviation value of the density values to serve as the second property value.

The property value set related to repeatability of data points of a 3D point cloud is obtained according to positions of the data points in each of the relevant images. In some embodiments, the first property value of the property value set related to repeatability of data points of a 3D point cloud is a fourth default value predetermined by the processing unit 5. In some embodiments, the processing unit 5 first obtains, for each of the relevant images, a density value related to distribution of the data points of the 3D point cloud, and then calculates a standard deviation value of the density values respectively of the relevant images to serve as the second property value of the property value set related to repeatability of data points of a 3D point cloud.

For the property value set related to error of the image from the actual data, the processing unit 5 first obtains, for each of the relevant images, an error value related to error points on the relevant image that are different from actual data and to distribution of the error points, and then calculates an average value of the error values respectively of the relevant images to serve as the first property value, and calculates a standard deviation value of the error values to serve as the second property value.

Further, steps 51-53 can be considered as a training phase for obtaining the initial image property data set for the article to be inspected in each of the initial projecting modes. In practice, the training phase of steps 51-53 can be implemented for different articles to be inspected, and a training result for each article (i.e., the initial image property data sets) is stored in the storage device 2. By this way, a user can learn the image properties of an image of a new article illuminated by the light source 3 in different projecting modes, and can select a suitable projecting mode for the new article accordingly.

It should be noted that the above-mentioned image properties are well known to those skilled in the art, and a property value thereof can be obtained based on various well-known algorithms or models. This disclosure is not limited to the foregoing exemplary description of the image properties and the calculations thereof.

In step 54, the processing unit 5 selects a candidate image property data set from the initial image property data sets according to a screening condition. The screening condition is related to the article and to at least one of the image properties, and is received by the processing unit 5 from the input module 1. For example, the input module 1 is a keyboard and/or a mouse operable by a user to input the screening condition.

Then, in step 55, the processing unit 5 further selects one of the initial projecting modes that corresponds to the candidate image property data set, and further selects one of the initial light source parameter sets that corresponds to the selected initial projecting mode as the candidate light source parameter set.

Figure 3:
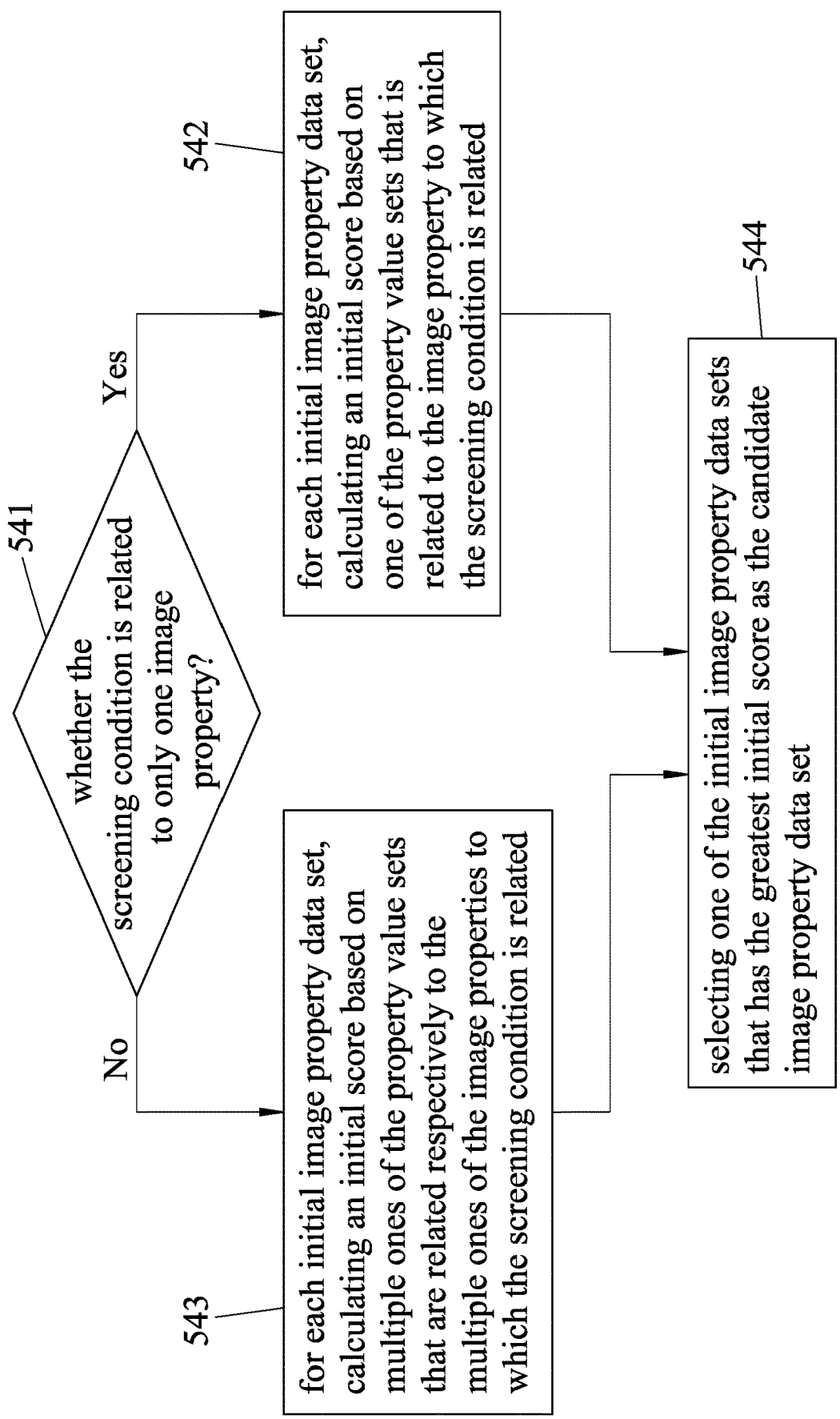
FIG. 3 is a flowchart illustrating detailed steps of the candidate selection procedure according to one embodiment of this disclosure.

Referring to FIG. 3, step 54 includes the following sub-steps 541 to 544 according to some embodiments of this disclosure.

In response of receipt of the screening condition, the processing unit 5 analyzes the screening condition to determine whether the screening condition is related to only one of the image properties in sub-step 541.

When it is determined that the screening condition is related to only one of the image properties (e.g., related only to image contrast), the flow goes to sub-step 542. When it is determined that the screening condition is related to multiple ones of the image properties (e.g., image contrast and image stability), the flow goes to sub-step 543.

In sub-step 542, for each of the initial image property data sets, the processing unit 5 calculates an initial score based on one of the property value sets of the initial image property data set according to the following equation (I). It should be noted that said one of the property value sets of the initial image property data set is related to said one of the image properties that the screening condition is related to.

$$V_S = u_1 \times V + u_2 \times V \times \sigma \qquad (1)$$

In equation (1), $V_S$ is the initial score, $u_1$ and $u_2$ are weights respectively for the first and second property values, V is the first property value included in said one of the property value sets, and $\sigma$ is the second property value included in said one of the property value sets.

In the case that the screening condition is related to multiple ones of the image properties, the screening condition has a plurality of weights for the multiple ones of the image properties, respectively. In sub-step 543, for each of the initial image property data sets, the processing unit 5 calculates the initial score based on multiple ones of the property value sets of the initial image property data set according to the following equation (2). It should be noted that the multiple ones of the property value sets of the initial image property data set are related respectively to the multiple ones of the image properties that the screening condition is related to.

$$V_S = \sum_{n=1}^{N} W_n(u_1 \times V_n + u_2 \times V_n \times \sigma_n) \qquad (2)$$

In equation (2) N is a number of the multiple ones of the image properties, $W_n$ is a weight for an $n^{th}$ one of the multiple ones of the image properties, V is the first property value included in an $n^{th}$ one of the multiple ones of the property value sets that is related to the $n^{th}$ one of the multiple ones of the image properties, and $\sigma_n$ is the second property value included in the $n^{th}$ one of the multiple ones of the property value sets.

Then, in sub-step 544, the processing unit 5 selects one of the initial image property data sets that has the greatest initial score as the candidate image property data set.

Figure 4:
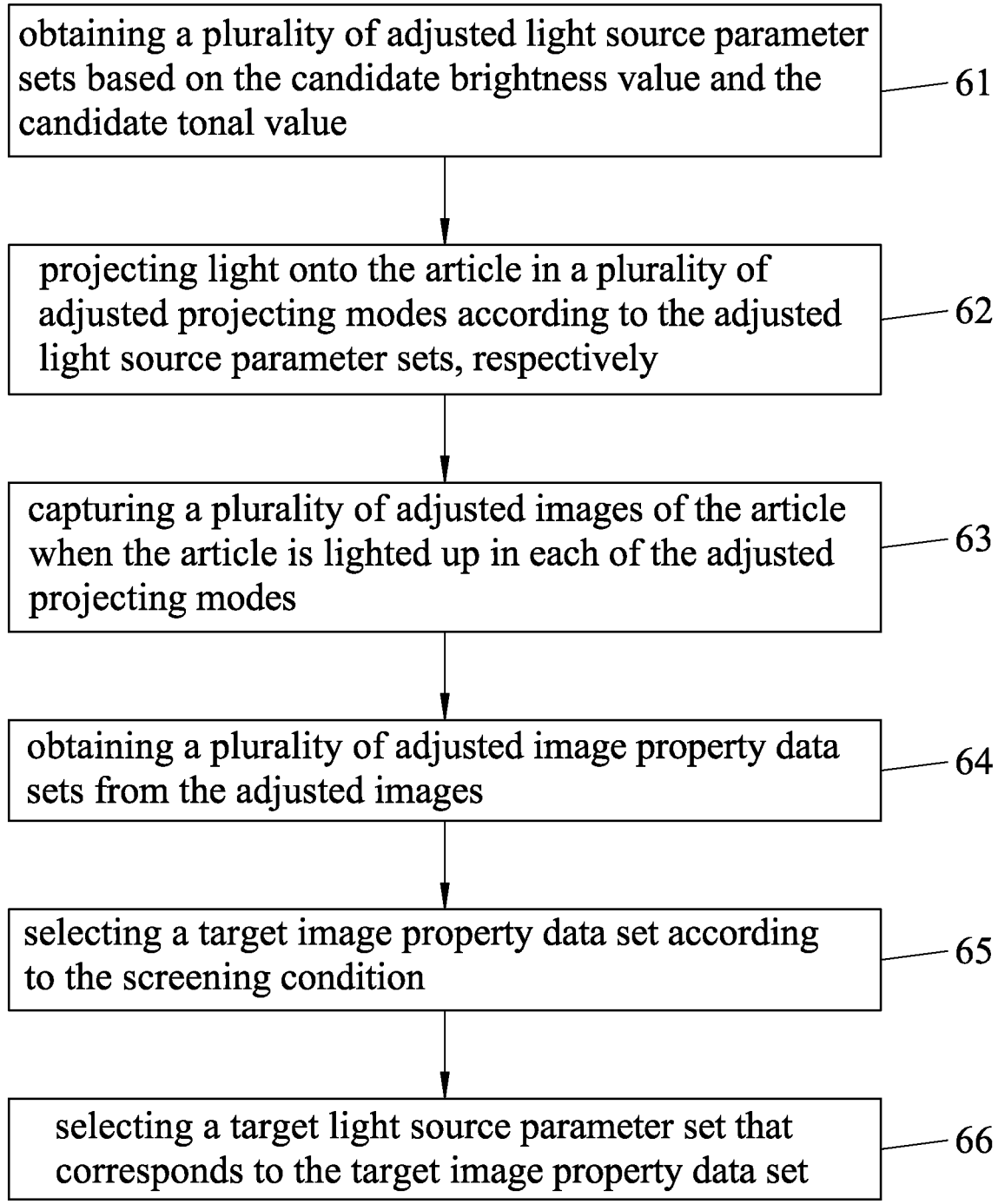
FIG. 4 is a flowchart of a target selection procedure of the adaptive method according to one embodiment of this disclosure.

Referring to FIG. 4, the target selection procedure is to select a target light source parameter set (i.e., selecting a target projecting mode), and includes the following steps 61 to 66.

In step 61, the processing unit 5 obtains a plurality of adjusted light source parameter sets based on the initial brightness value and the initial tonal value included in the candidate light source parameter sets Hereinafter, the initial brightness value and the initial tonal value included in the candidate light source parameter set are referred to as the candidate brightness value and the candidate tonal value, respectively.

Figure 5:
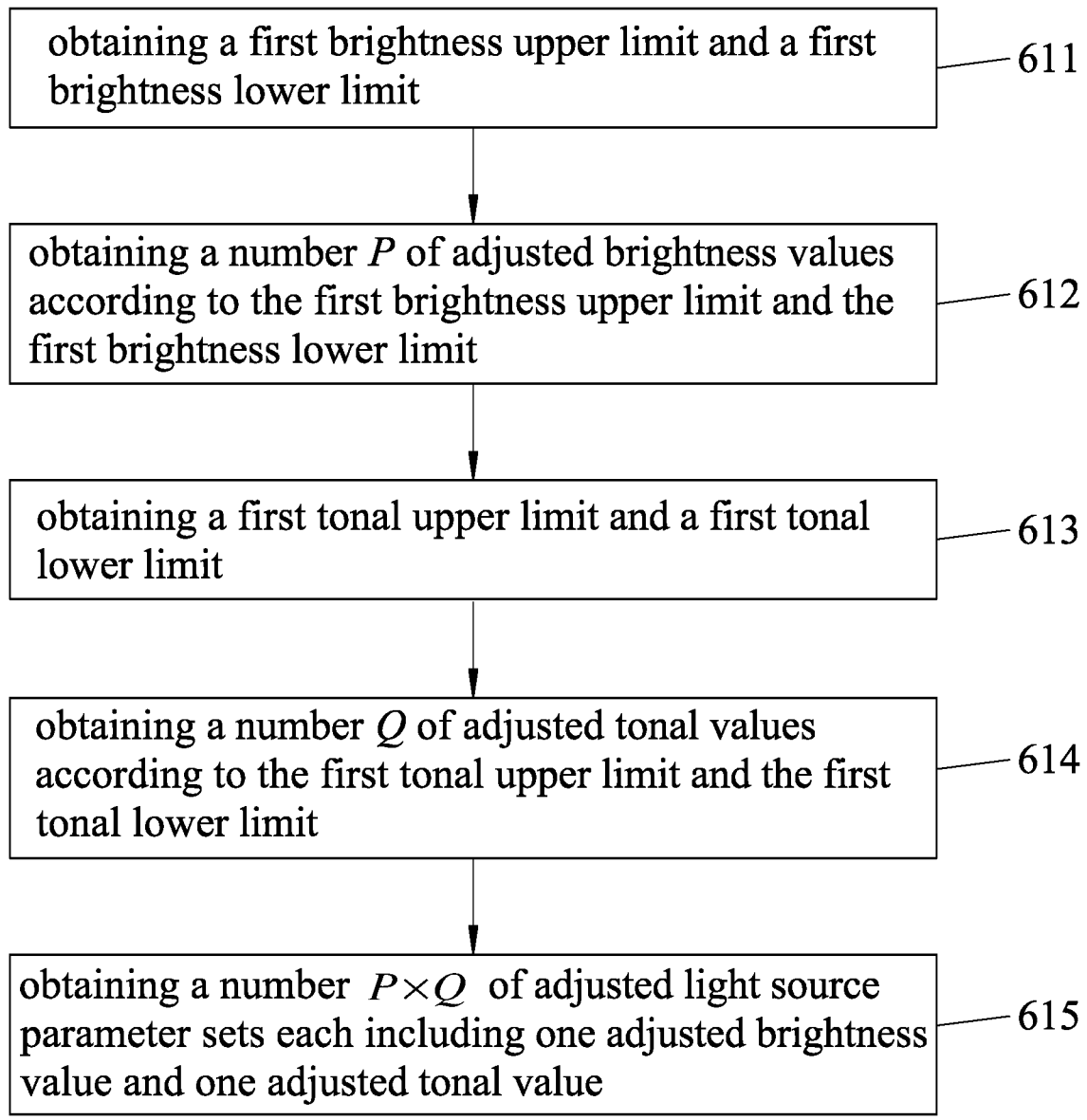
FIGS. 5 and 6 are flowcharts illustrating detailed steps of the target selection procedure according to some embodiments of this disclosure.

Further referring to FIG. 5, step 61 includes the following sub-steps 611 to 615 according to some embodiments of this disclosure.

In sub-step 611, the processing unit 5 obtains a first brightness upper limit and a first brightness lower limit based on the candidate brightness value and a first allowable brightness variation. Then, in sub-step 612, the processing unit 5 obtains a number P of adjusted brightness values according to the first brightness upper limit and the first brightness lower limit, where P≥1. In sub-step 613, the processing unit 5 obtains a first tonal upper limit and a first tonal lower limit based on the candidate tonal value and a first allowable tonal variation. Then, in sub-step 614, the processing unit 5 obtains a number Q of adjusted tonal values according to the first tonal upper limit and the first tonal lower limit, where Q≥1. In sub-step 615, the processing unit 5 obtains a number P×Q of the adjusted light source parameter sets each including one of the adjusted brightness values and one of the adjusted tonal values and each being a distinct combination of one of the adjusted brightness values and one of the adjusted tonal values. The first allowable brightness variation and the first allowable tonal variation are predetermined values and, are determined according to practical demand. In one embodiment, the first brightness upper limit is obtained by adding the first allowable brightness variation to the candidate brightness value, and the first brightness lower limit is obtained by subtracting the first allowable brightness variation from the candidate brightness value. In one embodiment, the first tonal upper limit is obtained by adding the first allowable tonal variation to the candidate tonal value, and the first tonal lower limit is obtained by subtracting the first allowable tonal variation from the candidate tonal value.

For example, the candidate brightness value and the candidate tonal value included in the candidate light source parameter set are 90 and 110, respectively, and the first allowable brightness variation and the first allowable tonal variation are 30 and 40, respectively. The first brightness upper limit is equal to 90+30=120, and the first brightness lower limit is equal to 90−30=60. The first tonal upper limit is equal to 110+40=150, and the first tonal lower limit is equal to 110−40=70. In one embodiment, the first brightness upper limit and the first brightness lower limit compose a half-open interval (e.g., a left-open interval), and the first tonal upper limit and the first tonal lower limit compose a half-open interval (e.g., a left-open interval). Accordingly, sixty adjusted brightness values (integers ranging from 61 to 120) are obtained, and eighty adjusted tonal values (integers ranging from 71 to 150) are obtained, i.e., P=60 and Q=80. As a result, a total number 60×80 of adjusted light source parameter sets are obtained, and each includes a combination of one of the adjusted brightness values and one of the adjusted tonal values. Namely, the adjusted light source parameter sets include [61, 71], [61, 72], ..., [61, 150], [62, 71], [62, 72], ..., [62, 150], ..., [120, 71], [120, 72], ..., [120, 150], where each square bracket is used to represent one of the adjusted light source parameter sets, in which the former number in the square bracket represents one of the adjusted brightness values, and the latter number in the square bracket represents one of the adjusted tonal values.

In step 62, the processing unit 5 controls the light source 3 to project light onto the article in a plurality of adjusted projecting modes according to the adjusted light source parameter sets, respectively.

In step 63, the image capturing device 4 captures a plurality of adjusted images of the article when the article is lighted up by the light source 3 in each of the adjusted projecting modes.

In step 64, the processing unit 5 obtains a plurality of adjusted image property data sets. Each of the adjusted image property data sets is obtained from the adjusted images that are captured in a respective one of the adjusted projecting modes, and includes a plurality of property value sets that are related to the image properties, respectively. Each of the property value sets of each adjusted image property data set includes a third property value and a fourth property value that are related to one of the image properties corresponding to the property value set. The manner for obtaining the third property value is similar to that for obtaining the first property value, and the manner for obtaining the fourth property value is similar to that for obtaining the second property value. In some embodiments, the third property value is, but not limited to, an average value. In some embodiments, the fourth property value is, but not limited to, a standard deviation value.

It should be noted that, in one embodiment, the processing unit 5 obtains all of the adjusted light source parameter sets at once, and then obtains all of the adjusted image property data sets corresponding respectively to the adjusted projecting modes. In other embodiments, the processing unit 5 obtains only one adjusted light source parameter set at a time, and subsequently obtains one adjusted image property data set corresponding to the adjusted projecting mode related to said one of the adjusted light source parameter set, and then repeats the steps for obtaining another adjusted light source parameter set and obtaining a corresponding adjusted image property data set, until all of the adjusted image property data sets corresponding respectively to all of the adjusted projecting modes are obtained.

In step 65, the processing unit 5 selects a target image property data set from the adjusted image property data sets according to the screening condition. Then, in step 66, the processing unit 5 further selects one of the adjusted light source parameter sets that corresponds to the target image property data set as the target light source parameter set.

Figure 6:
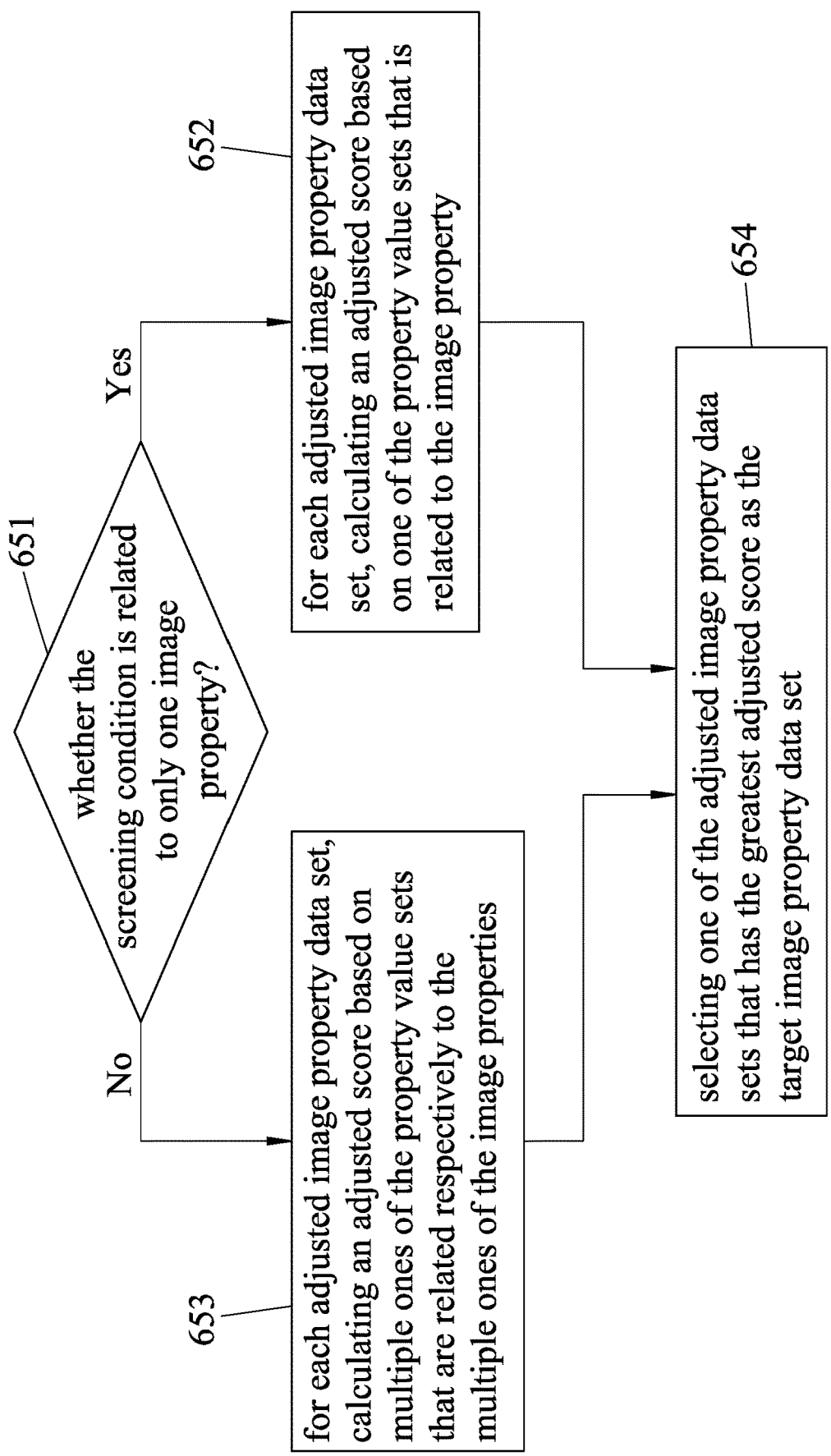

Further referring to FIG. 6, step 65 includes the following sub-steps 651 to 654 according to some embodiments of this disclosure.

In sub-step 651, the processing unit 5 analyzes the screening condition to determine whether the screening condition is related to only one of the image properties. The flow goes to sub-step 652 when it is determined that the screening condition is related to only one of the image properties, and goes to sub-step 653 when it is determined that the screening condition is related to multiple ones of the image properties.

In sub-step 652, for each of the adjusted image property data sets, the processing unit 5 calculates an adjusted score based on one of the property value sets of the adjusted image property data set according to the following equation (3). It should be noted that said one of the property value sets of the adjusted image property data set is related to said one of the image properties that the screening condition is related to.

$$V'_S = u_1 \times V' + u_2 \times V' \times \sigma' \qquad (3)$$

In equation (3), $V'_S$ is the adjusted score, $u_1$ and $u_2$ are weights respectively for the third and fourth property values, $V'$ is the third property value included in said one of the property value sets, and $\sigma'$ is the fourth property value included in said one of the property value sets.

In sub-step 653, for each of the adjusted image property data sets, the processing unit 5 calculates the adjusted score based on multiple ones of the property value sets of the adjusted image property data set according to the following equation (4). It should be noted that the multiple ones of the property value sets of the adjusted image property data set are related respectively to the multiple ones of the image properties that the screening condition is related to.

$$V'_S = \sum_{n=1}^{N} W_n (u_1 \times V'_n + u_2 \times V'_n \times \sigma'_n) \qquad (4)$$

In equation (4), $V'_n$ is the third property value included in an $n^{th}$ one of the multiple ones of the property value sets that is related to an $n^{th}$ one of the multiple ones of the image properties, and $\sigma'_n$ is the fourth property value included in the $n^{th}$ one of the multiple ones of the property value sets.

In sub-step 654, the processing unit 5 selects one of the adjusted image property data sets that has the greatest adjusted score as the target image property data set.

Figure 7:
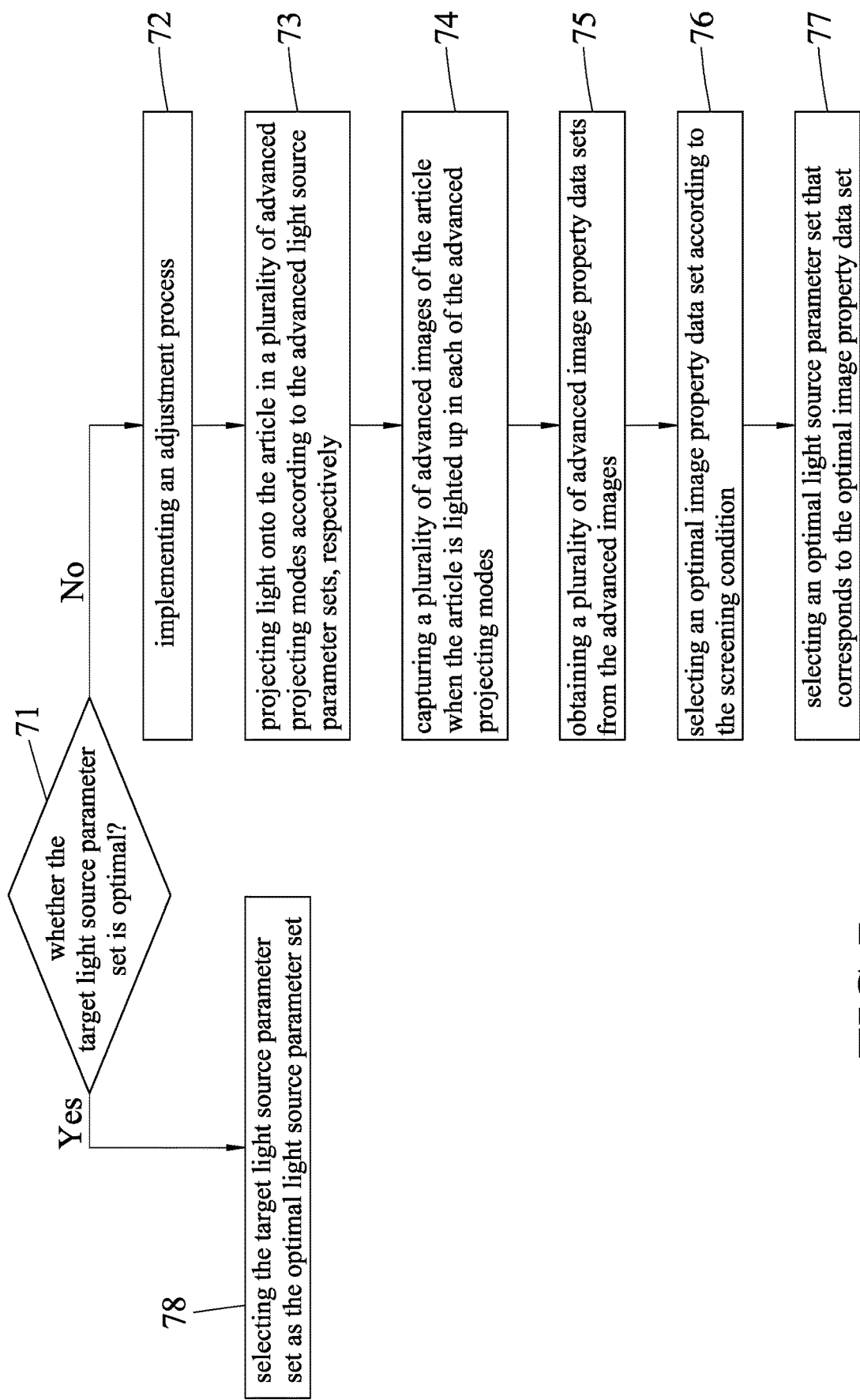
FIG. 7 is a flowchart of an optimization procedure of the adaptive method according to one embodiment of this disclosure.

Referring to FIG. 7, the optimization procedure is to select an optimal light source parameter set (i.e. selecting an optimal projecting mode), and includes the following steps 71 to 78.

In step 71, according to the adjusted brightness value and the adjusted tonal value included in the target light source parameter set, the first brightness upper limit, the first brightness lower limit, the first tonal upper limit and the first tonal lower limit, the processing unit 5 analyzes the target light source parameter set to determine whether the target light source parameter set is optimal. When it is determined that the target light source parameter set is not optimal, the flow goes to step 72 to implement an adjustment process based on the target light source parameter set. When it is determined that the target light source parameter set is optimal, the flow goes to step 78, in which the processing unit 5 selects the target light source parameter set as the optimal light source parameter set. Hereinafter, the adjusted brightness value and the adjusted tonal value included in the target light source parameter set are referred to as the target brightness value and the target tonal value, respectively.

Figure 8:
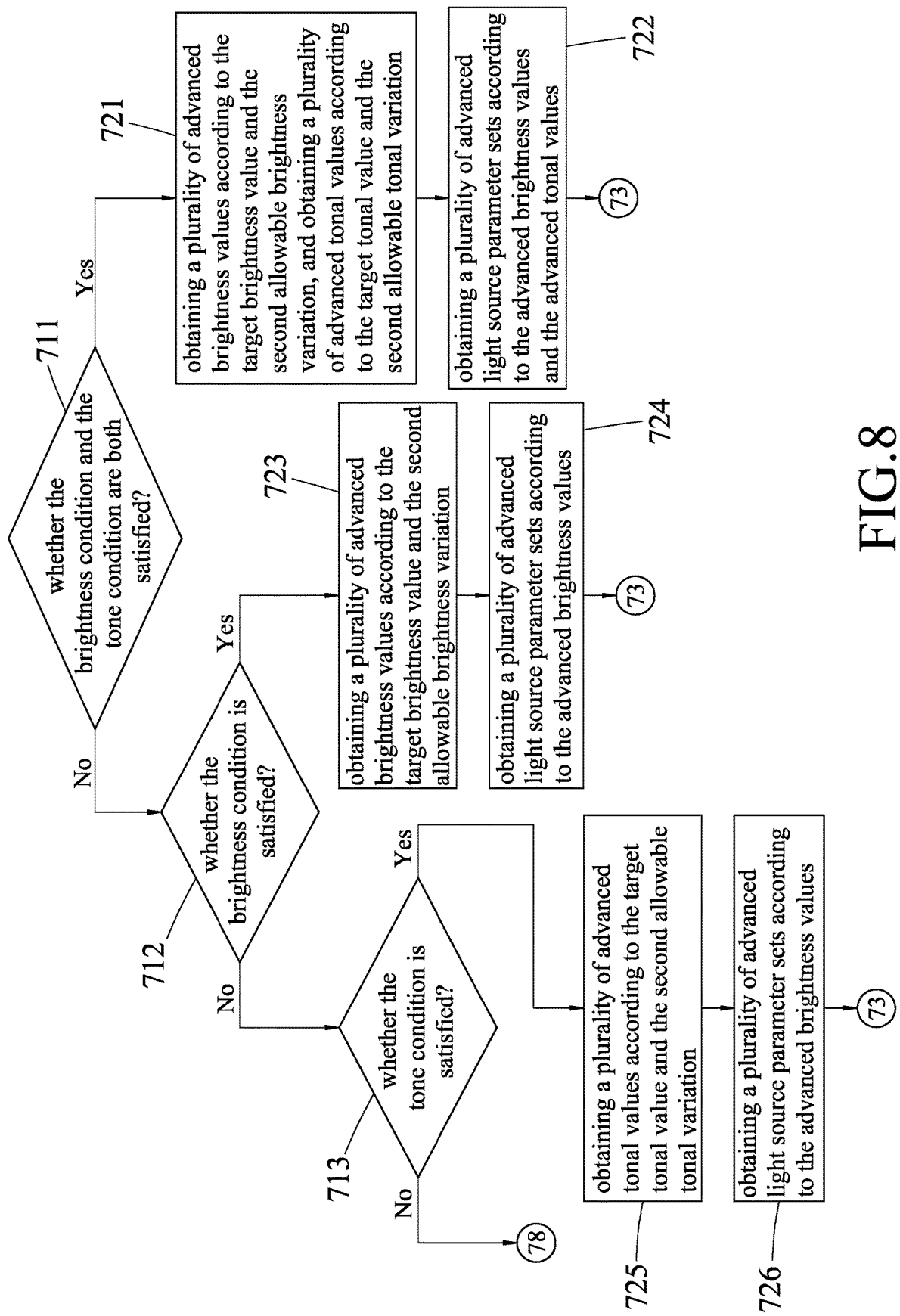
FIGS. 8 and 9 are flowcharts illustrating detailed steps of the optimal selection procedure according to some embodiments of this disclosure.

Further referring FIG. 8, step 71 includes sub-steps 711 to 713 according to some embodiments of this disclosure. Step 72 includes three different adjustment processes (i.e. sub-steps 721 and 722, sub-steps 723 and 724, and sub-steps 725 and 726) to be implemented according to a result of the determination of step 71.

In sub-step 711, the processing unit 5 analyzes the target light source parameter set to determine whether a brightness condition that the target brightness value is equal to the first brightness upper limit or the first brightness lower limit and a tone condition that the target tonal value is equal to the first tonal upper limit or the first tonal lower limit are both satisfied. When the processing unit 5 determines that the brightness condition and the tone condition are both satisfied, the flow goes to sub-step 721 to implement a first adjustment process based on the target light source parameter set. The flow goes to sub-step 712 when otherwise.

In sub-step 712, the processing unit 5 determines whether the brightness condition that the target brightness value is equal to the first brightness upper limit or the first brightness lower limit is satisfied. When it is determined that the target brightness value is equal to the first brightness upper limit or equal to the first brightness lower limit, the flow goes sub-step 723 to implement a second adjustment process based on the target light source parameter set. When it is determined that the target brightness value equals to neither the first brightness upper limit nor the first brightness lower limit, the flow goes to sub-step 713.

In sub-step 713, the processing unit 5 determines whether the tone condition that the target tonal value is equal to the first tonal upper limit or the first tonal lower limit is satisfied. When it is determined that the target tonal value is equal to the first tonal upper limit or equal to the first tonal lower limit, the flow goes sub-step 725 to implement a third adjustment process based on the target light source parameter set. When it is determined that the target tonal value equals neither the first tonal upper limit nor the first tonal lower limit, the flow goes to step 78, in which the processing unit 5 selects the target light source parameter set as the optimal light source parameter set.

In response to the result of the determination of step 71 that the brightness condition and the tone condition are both satisfied, the processing unit 5 implements the first adjustment process having sub-steps 721 and 722. In response to the result of the determination of step 71 that the brightness condition is satisfied and the tone condition is not satisfied, the processing unit 5 implements the second adjustment process having sub-steps 723 and 724. In response to the result of the determination of step 71 that the brightness condition is not satisfied and the tone condition is satisfied, the processing unit 5 implements the third adjustment process having sub-steps 725 and 726. In response to the result of the determination of step 71 that neither the brightness condition nor the tone condition is satisfied, the processing unit 5 implements step 78 to select the target light source parameter set as the optimal light source parameter set.

In the first adjustment process, the processing unit 5 first analyzes the target brightness value and the target tonal value. When it is determined that the target brightness value is equal to the first brightness upper limit and the target tonal value is equal to the first tonal upper limit, in sub-step 721, the processing unit 5 obtains a second brightness upper limit based on the target brightness value and a second allowable brightness variation, obtains a number R of advanced brightness values according to the target brightness value and the second brightness upper limit, obtains a second tonal upper limit based on the target brightness value and a second allowable tonal variation, and obtains a number T of advanced tonal values according to the target tonal value and the second tonal upper limit, Subsequently, in sub-step 722, the processing unit 5 obtains a number R×T of advanced light source parameter sets each including one of the advanced brightness values and one of the advanced tonal values, and each being a distinct combination of the advanced brightness values and the advanced tonal values. Then, the flow goes to step 73.

When it is determined that the target brightness value is equal to the first brightness upper limit and the target tonal value is equal to the first tonal lower limit, in sub-step 721, the processing unit 5 obtains a second brightness upper limit based on the target brightness value and the second allowable brightness variation, obtains a number R of advanced brightness values according to the target brightness value and the second brightness upper limit, obtains a second tonal lower limit based on the target tonal value and the second allowable tonal variation, and obtains a number U of advanced tonal values according to the target tonal value and the second tonal lower limit. Subsequently, in sub-step 722, the processing unit 5 obtains a number R×U of advanced light source parameter sets each including one of the advanced brightness values and one of the advanced tonal values, and each being a distinct combination of the advanced brightness values and the advanced tonal values. Then, the flow goes to step 73.

When it is determined that the target brightness value is equal to the first brightness lower limit and the target tonal value is equal to the first tonal upper limit, in sub-step 721, the processing unit 5 obtains a second brightness lower limit based on the target brightness value and the second allowable brightness variation, obtains a number S of advanced brightness values according to the target brightness value and the second brightness lower limit, obtains a second tonal upper limit based on the target brightness value and the second allowable tonal variation, and obtains a number T of advanced tonal values according to the target tonal value and the second tonal upper limit. Subsequently, in sub-step 722, the processing unit 5 obtains a number S×T of advanced light source parameter sets each including one of the advanced brightness values and one of the advanced tonal values, and each being a distinct combination of the advanced brightness values and the advanced tonal values. Then, the flow goes to step 73.

When it is determined that the target brightness value is equal to the first brightness lower limit and the target tonal value is equal to the first tonal lower limit, in sub-step 721, the processing unit 5 obtains a second brightness lower limit based on the target brightness value and the second allowable brightness variation, obtains a number S of advanced brightness values according to the target brightness value and the second brightness lower limit, obtains a second tonal lower limit based on the target brightness value and the second allowable tonal variation, and obtains a number U of advanced tonal values according to the target tonal value and the second tonal lower limit.

Subsequently, in sub-step 722, the processing unit 5 obtains a number S×U of advanced light source parameter sets each including one of the advanced brightness values and one of the advanced tonal values, and each being a distinct combination of the advanced brightness values and the advanced tonal values. Then, the flow goes to step 73.

It should be noted that, in some embodiments, each of the numbers R, S, T and U may be equal to or greater than one; that is to say, there may be cases where only one advanced brightness value and/or only one advanced tonal value is obtained.

For example, the target brightness value and the target tonal value of the target light source parameter set are 150 and 120, respectively, and the first brightness upper limit and the first tonal upper limit are also 150 and 120, respectively. Accordingly, the first adjustment process having sub-steps 721 and 722 is implemented. The second allowable brightness variation and the second allowable tonal variation are predetermined values, and are, for example, 20 and 30, respectively. The second brightness upper limit would then equal 150+20=170, and the second tonal upper limit would then equal 120+30=150. In one embodiment, the target brightness value (150) and the second brightness upper limit (170) compose a half-open interval (e.g., a left-open interval), and the target tonal value (120) and the second tonal upper limit (150) compose a half-open interval (e.g., a left-open interval). Accordingly, twenty advanced brightness values (integers ranging from 151 to 170) are obtained, and thirty advanced tonal values (integers ranging from 121 to 150) are obtained, i.e., R=20 and T=30. As a result, a total number 20×30 of the advanced light source parameter sets are obtained, each of which includes a combination of one of the advanced brightness values and one of the advanced tonal values. Namely, the advanced light source parameter sets include [151, 121], [151, 122], . . . , [151, 150], [152, 121], [152, 122], . . . , [152, 150], . . . , [170, 121], [170, 122], . . . , [170, 150], where each square bracket is used to represent one of the advanced light source parameter sets, in which the former number in the square bracket represents one of the advanced brightness values, and the latter number in the square bracket represents one of the advanced tonal values.

In some embodiments, the second brightness lower limit is obtained by subtracting the second allowable brightness variation from the target brightness value, and the second tonal lower limit is obtained by subtracting the second allowable tonal variation from the target tonal value.

As for the second adjustment process, the processing unit 5 first analyzes the target brightness value to determine which of the first brightness upper limit and the first brightness lower limit the target brightness value is equal to. When it is determined that the target brightness value is equal to the first brightness upper limit, in sub-step 723, the processing unit 5 obtains a second brightness upper limit based on the target brightness value and the second allowable brightness variation, and obtains a number R of advanced brightness values according to the target brightness value and the second brightness upper limit. Subsequently, in sub-step 724, the processing unit 5 obtains a number R×1 of advanced light source parameter sets each including the target tonal value and a respective one of the advanced brightness values. Then, the flow goes to step 73.

When it is determined that the target brightness value is equal to the first brightness lower limit, in sub-step 723, the processing unit 5 obtains a second brightness lower limit based on the target brightness value and the second allowable brightness variation, and obtains a number S of advanced brightness values according to the target brightness value and the second brightness lower limit. Subsequently, in sub-step 724, the processing unit 5 obtains a number S×1 of advanced light source parameter sets each including the target tonal value and a respective one of the advanced brightness values. Then, the flow goes to step 73.

As for the third adjustment process, the processing unit 5 first analyzes the target tonal value of the target light source parameter set to determine which of the first tonal upper limit and the first tonal lower limit the target tonal value is equal to. When it is determined that the target tonal value is equal to the first tonal upper limit, in sub-step 725, the processing unit 5 obtains a second tonal upper limit based on the target tonal value and the second allowable tonal variation, and obtains a number T of advanced tonal values according to the target tonal value and the second tonal upper limit. Subsequently, in sub-step 726, the processing unit 5 obtains a number T×1 of the advanced light source parameter sets each including the target brightness valued and a respective one of the advanced tonal values. Then, the flow goes to step 73.

When it is determined that the target tonal value is equal to the first tonal lower limit, in sub-step 725, the processing unit 5 obtains a second tonal lower limit based on the target tonal value and the second allowable tonal variation, and obtains a number U of advanced tonal values according to the target tonal value and the second tonal lower limit. Subsequently, in sub-step 726, the processing unit 5 obtains a number U×1 of advanced light source parameter sets each including the target brightness valued and a respective one of the advanced tonal values. Then, the flow goes to step 73.

In step 73, the processing unit 5 controls the light source 3 to project light onto the article in a plurality of advanced projecting modes according to the advanced light source parameter sets, respectively.

In step 74, the image capturing device 4 captures a plurality of advanced images of the article when the article is lighted up by the light source 3 in each of the advanced projecting modes.

In step 75, the processing unit 5 obtains a plurality of advanced image property data sets. Each of the advanced image property data sets is obtained from the advanced images that are captured in a respective one of the advanced projecting modes, and includes a plurality of property value sets that are related to the image properties, respectively. Each of the property value sets of each advanced image property data set includes a fifth property value and a sixth property value that are related to one of the image properties to which the property value set is related. The manner for obtaining the fifth property value is similar to that for obtaining the first property value, and the manner for obtaining the sixth property value is similar to that for obtaining the second property value. In some embodiments, the fifth property value is, but not limited to, an average value. In some embodiments, the sixth property value is, but not limited to, a standard deviation value.

In step 76, the processing unit 5 selects an optimal image property data set from the advanced image property data sets according to the screening condition. Then, in step 77, the processing unit 5 selects one of the advanced light source parameter sets that corresponds to the optimal image property data set to serve as the optimal light source parameter set.

Figure 9:
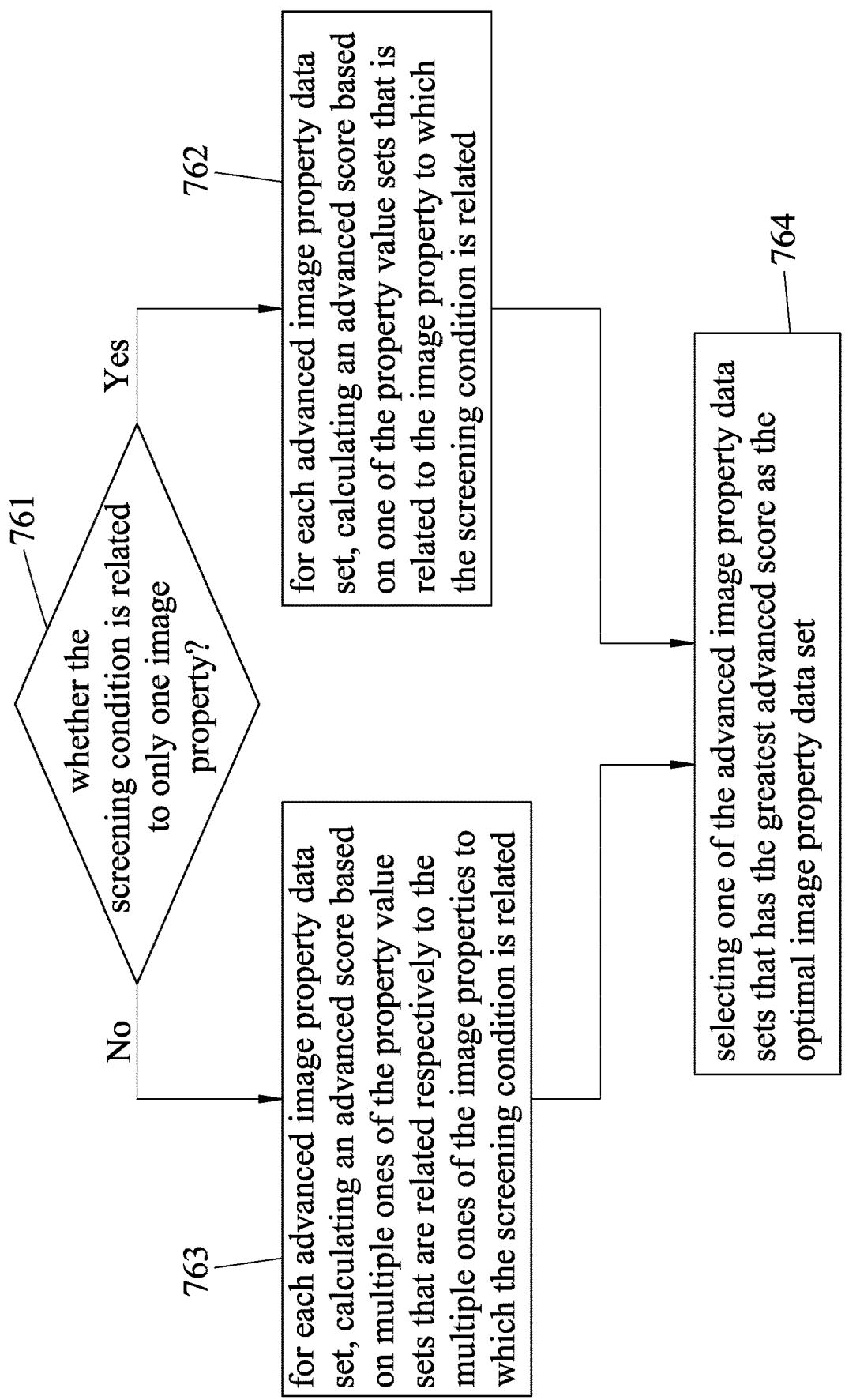

Further referring to FIG. 9, step 76 includes the following sub-steps 761 to 764 according to some embodiments of this disclosure.

In sub-step 761, the processing unit 5 analyzes the screening condition to determine whether the screening condition is related to only one of the image properties. The flow goes to sub-step 762 when it is determined that the screening condition is related to only one of the image properties, and goes to sub-step 763 when it is determined that the screening condition is related to multiple ones of the image properties.

In sub-step 762, for each of the advanced image property data sets, the processing unit 5 calculates an advanced score based on one of the property value sets of the advanced image property data set according to the following equation (5). It should be noted that said one of the property value sets of the advanced image property data set is related to said one of the image properties that the screening condition is related to.

$$V''_S = u_1 \times V'' + u_2 \times V'' \times \sigma'' \quad (5)$$

In equation (5), $V''_S$ is the advanced score, $V''$ is the fifth property value included in said one of the property value sets, and $\sigma''$ is the sixth property value included in said one of the property value sets.

In sub-step 763, for each of the advanced image property data sets, the processing unit 5 calculates the advanced score based on multiple ones of the property value sets of the advanced image property data set according to the following equation (6). It should be noted that the multiple ones of the property value sets of the advanced image property data set are related respectively to the multiple ones of the image properties that the screening condition is related to.

$$V''_S = \sum_{n=1}^{N} W_n(u_1 \times V''_n + u_2 \times V''_n \times \sigma''_n) \quad (6)$$

In equation (6), $V''_n$ is the fifth property value included in an $n^{th}$ one of the multiple ones of the property value sets that is related to an $n^{th}$ one of the multiple ones of the image properties, and $\sigma''_n$ is the sixth property value included in the $n^{th}$ one of the multiple ones of the property value sets.

In sub-step 764, the processing unit 5 selects one of the advanced image property data sets that has the greatest advanced score as the optimal image property data set.

It should be noted that, although the steps and sub-steps in the flowcharts are shown in a particular order, the order of these steps can be modified. Thus, the illustrated embodiments can be performed with a different order of steps, and some steps may be performed in parallel.

In one embodiment, the adaptive method further includes steps of the processing unit 5 controlling the light source 3 to project light onto the article in the target projecting mode according to the target light source parameter set, the image capturing device 4 capturing a plurality of images of the article when the article is lighted up by the light source 3 in the target projecting mode, and the processing unit 5 analyzing the images captured in the target projecting mode to inspect the article.

In one embodiment, the adaptive method further includes steps of the processing unit 5 controlling the light source 3 to project light onto the article in the optimal projecting mode according to the optimal light source parameter set, the image capturing device 4 capturing a plurality of images of the article when the article is lighted up by the light source 3 in the optimal projecting mode, and the processing unit 5 analyzing the images captured in the optimal projecting mode to inspect the article.

In sum, the adaptive method for a light source according to some embodiments of this disclosure selects one of the initial image property data sets that has the greatest initial score as the candidate image property data set. Then, the processing unit 5 obtains a plurality of adjusted light source parameter sets based on the candidate brightness value and the candidate tonal value of the candidate light source parameter set, and selects one of the adjusted light source parameter sets that has the greatest adjusted score as the target image property data set. Accordingly, when the article is lighted up by the light source 3 in the target projecting mode, the images of the article captured by the image capturing device 4 may have relatively better image properties. Moreover, when it is determined that optimization may be required for the target light source parameter set (i.e., the brightness condition or the tone condition is satisfied) the processing unit 5 obtains a plurality of advanced light source parameter sets based on the target brightness value and the target tonal value of the target light source parameter set, and selects one of the advanced light source parameter sets that has the greatest advanced score as the optimal image property dataset. Accordingly, when the article is lighted up by the light source 3 in the optimal projecting mode, the images of the article captured by the image capturing device 4 may have the best image properties, so that inspection of the article based on these images may be relatively accurate.

In the description above, for the purposes of explanation, numerous specific details have been set forth in order to provide a thorough understanding of the embodiments. It will be apparent, however, to one skilled in the art, that one or more other embodiments may be practiced without some of these specific details.

It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. An adaptive method for a light source that is used for inspecting an article, the adaptive method to be implemented using an automatic adapting system that includes a storage device, a light source, an image capturing device and a processing unit, the light source being configured to project light onto the article in a plurality of initial projecting modes, the storage device storing a plurality of initial light source parameter sets corresponding respectively to the initial projecting modes, and a plurality of initial image property data sets each being obtained by illuminating the article in a respective one of the initial projecting modes and each including a plurality of property value sets that are related respectively to a plurality of image properties, the adaptive method comprising steps of:

selecting, by the processing unit, a candidate image property data set from the initial image property data sets according to a screening condition, the screening condition being related to the article and to at least one of the image properties;

selecting, by the processing unit, a candidate light source parameter set that corresponds to the candidate image property data set from the initial light source parameter sets;

obtaining, by the processing unit, a plurality of adjusted light source parameter sets based on the candidate light source parameter set;

controlling, by the processing unit, the light source to project light onto the article in a plurality of adjusted projecting modes according to the adjusted light source parameter sets, respectively;

capturing, by the image capturing device, a plurality of adjusted images of the article when the article is lighted up by the light source in each of the adjusted projecting modes;

obtaining, by the processing unit, a plurality of adjusted image property data sets each being obtained from the adjusted images that are captured in a respective one of the adjusted projecting modes, and each including a plurality of property value sets that are related respectively to the image properties;

selecting, by the processing unit, a target image property data set from the adjusted image property data sets according to the screening condition; and selecting, by the processing unit, a target light source parameter set that corresponds to the target image property data set from the adjusted light source parameter sets;

wherein the step of selecting a candidate image property data set includes:

when the screening condition is related to only one of the image properties, for each of the initial image property data sets, calculating an initial score based on one of the property value sets of the initial image property data set according to $V_S = u_1 \times V + u_2 \times V \times \sigma$, where $V_S$ is the initial score, $u_1$ and $u_2$ are weights, V is a first property value included in said one of the property value sets, and $\sigma$ is a second property value included in said one of the property value sets, said one of the property value sets being related to said one of the image properties to which the screening condition is related;

when the screening condition is related to multiple ones of the image properties and has a plurality of weights respectively for the multiple ones of the image properties, for each of the initial image property data sets, calculating the initial score based on multiple ones of the property value sets of the initial image property data set according to $$V_S = \sum_{n=1}^{N} W_n(u_1 \times V_n + u_2 \times V_n \times \sigma_n),$$

where N is a number of the multiple ones of the image properties, $W_n$ is a weight for an $n^{th}$ one of the multiple ones of the image properties, $V_n$ is the first property value included in an $n^{th}$ one of the multiple ones of the property value sets that is related to the $n^{th}$ one of the multiple ones of the image properties, and $\sigma_n$ is the second property value included in the $n^{th}$ one of the multiple ones of the property value sets, the multiple ones of the property value sets being related respectively to the multiple ones of the image properties to which the screening condition is related; and selecting one of the initial image property data sets that has the greatest initial score as the candidate image property data set.

2. The adaptive method of claim 1, wherein the step of obtaining a plurality of adjusted light source parameter sets based on the candidate light source parameter set includes obtaining a plurality of adjusted light source parameter sets based on calculations made on a candidate brightness value and a candidate tonal value included in the candidate light source parameter set.

3. The adaptive method of claim 1, further comprising, before the step of selecting a candidate light source parameter, steps of:

controlling, by the processing unit, the light source to project light onto the article in the initial projecting modes one by one, according to the corresponding one of the initial light source parameter sets;

capturing, by the image capturing device, a plurality of initial images of the article when the article is lighted up by the light source in each of the initial projecting modes;

obtaining, by the processing unit, the initial image property data sets each being obtained from the initial images that are captured in the respective one of the initial projecting modes; and storing, by the processing unit, the initial image property data sets in the storage device.

4. An adaptive method for a light source that is used for inspecting an article, the adaptive method to be implemented using an automatic adapting system that includes a storage device, a light source, an image capturing device and a processing unit, the light source being configured to project light onto the article in a plurality of initial projecting modes, the storage device storing a plurality of initial light source parameter sets corresponding respectively to the initial projecting modes, and a plurality of initial image property data sets each being obtained by illuminating the article in a respective one of the initial projecting modes and each including a plurality of property value sets that are related respectively to a plurality of image properties, the adaptive method comprising steps of:

selecting, by the processing unit, a candidate image property data set from the initial image property data sets according to a screening condition, the screening condition being related to the article and to at least one of the image properties;

selecting, by the processing unit, a candidate light source parameter set that corresponds to the candidate image property data set from the initial light source parameter sets;

obtaining, by the processing unit, a plurality of adjusted light source parameter sets based on the candidate light source parameter set;

controlling, by the processing unit, the light source to project light onto the article in a plurality of adjusted projecting modes according to the adjusted light source parameter sets, respectively;

capturing, by the image capturing device, a plurality of adjusted images of the article when the article is lighted up by the light source in each of the adjusted projecting modes;

obtaining, by the processing unit, a plurality of adjusted image property data sets each being obtained from the adjusted images that are captured in a respective one of the adjusted projecting modes, and each including a plurality of property value sets that are related respectively to the image properties;

selecting, by the processing unit, a target image property data set from the adjusted image property data sets according to the screening condition; and selecting, by the processing unit, a target light source parameter set that corresponds to the target image property data set from the adjusted light source parameter sets;

wherein the step of obtaining a plurality of adjusted light source parameter sets based on the candidate light source parameter set includes obtaining a plurality of adjusted light source parameter sets based on calculations made on a candidate brightness value and a candidate tonal value included in the candidate light source parameter set;

wherein the step of obtaining a plurality of adjusted light source parameter sets based on the candidate light source parameter set further includes:
    obtaining a first brightness upper limit and a first brightness lower limit based on the candidate brightness value and a first allowable brightness variation;
    obtaining a number P of adjusted brightness values according to the first brightness upper limit and the first brightness lower limit;
    obtaining a first tonal upper limit and a first tonal lower limit based on the candidate tonal value and a first allowable tonal variation;
    obtaining a number Q of adjusted tonal values according to the first tonal upper limit and the first tonal lower limit; and
    obtaining a number P×Q of the adjusted light source parameter sets each including one of the adjusted brightness values and one of the adjusted tonal values.

5. The adaptive method of claim 4, wherein, in the step of obtaining a first brightness upper limit and a first brightness lower limit, the first brightness upper limit is obtained by adding the first allowable brightness variation to the candidate brightness value, and the first brightness lower limit is obtained by subtracting the first allowable brightness variation from the candidate brightness value,
    wherein, in the step of obtaining a first tonal upper limit and a first tonal lower limit, the first tonal upper limit is obtained by adding the first allowable tonal variation to the candidate tonal value, and the first tonal lower limit is obtained by subtracting the first allowable tonal variation from the candidate tonal value.

6. The adaptive method of claim 4, wherein the step of selecting a target image property data set includes:
    when the screening condition is related to only one of the image properties, for each of the adjusted image property data sets, calculating an adjusted score based on one of the property value sets of the adjusted image property image property data set according to $V_S' = u_1 \times V' + u_2 \times V' \times \sigma'$, where $V_S'$ is the adjusted score, $u_1$ and $u_2$ are weights, $V'$ is a first property value included in said one of the property value sets, and $\sigma'$ is a second property value included in said one of the property value sets, said one of the property value sets being related to said one of the image properties to which the screening condition is related;
    when the screening condition is related to multiple ones of the image properties and has a plurality of weights respectively for the multiple ones of the image properties, for each of the adjusted image property data sets, calculating the adjusted score based on multiple ones of the property value sets of the adjusted image property data set according to $$V_S' = \sum_{n=1}^{N} W_n (u_1 \times V_n' + u_2 \times V_n' \times \sigma_n'),$$

where N is a number of the multiple ones of the image properties, $W_n$ is a weight for an $n^{th}$ one of the multiple ones of the image properties, $V_n'$ is the first property value included in an $n^{th}$ one of the multiple ones of the property value sets that is related to the $n^{th}$ one of the multiple ones of the image properties, and $\sigma_n'$ is the second property value included in the $n^{th}$ one of the multiple ones of the property value sets, the multiple ones of the property value sets being related respectively to the multiple ones of the image properties to which the screening condition is related; and
    selecting one of the adjusted image property data sets that has the greatest adjusted score as the target image property data set.

7. The adaptive method of claim 6, further comprising steps of:
    analyzing, by the processing unit, the adjusted brightness value included in one of the adjusted light source parameter sets that is selected as the target light source parameter set to determine whether the adjusted brightness value is equal to the first brightness upper limit;
    when the processing unit determines that the adjusted brightness value is equal to the first brightness upper limit, obtaining, by the processing unit, a second brightness upper limit based on the adjusted brightness value and a second allowable brightness variation;
    obtaining, by the processing unit, a plurality of advanced brightness values according to the adjusted brightness value and the second brightness upper limit;
    obtaining, by the processing unit, a plurality of advanced light source parameter sets each including one of the advanced brightness values;
    controlling, by the processing unit, the light source to project light onto the article in a plurality of advanced projecting modes according to the advanced light source parameter sets, respectively;
    capturing, by the image capturing device, a plurality of advanced images of the article when the article is lighted up by the light source in each of the advanced projecting modes;

obtaining, by the processing unit, a plurality of advanced image property data sets each being obtained from the advanced images that are captured in a respective one of the advanced projecting modes, and each including a plurality of property value sets that are related respectively to the image properties;

selecting, by the processing unit, an optimal image property data set from the advanced image property data sets according to the screening condition; and selecting, by the processing unit, an optimal light source parameter set that corresponds to the optimal image property data set from the advanced light source parameter sets.

8. The adaptive method of claim 7, wherein in the step of obtaining a second brightness upper limit, the second brightness upper limit is obtained by adding the second allowable brightness variation to the adjusted brightness value.

9. The adaptive method of claim 6, further comprising steps of:

analyzing, by the processing unit, the adjusted brightness value included in one of the adjusted light source parameter sets that is selected as the target light source parameter set to determine whether the adjusted brightness value is equal to the first brightness lower limit;

when the processing unit determines that the adjusted brightness value is equal to the first brightness lower limit, obtaining, by the processing unit, a second brightness lower limit based on the adjusted brightness value and a second allowable brightness variation;

obtaining, by the processing unit, a plurality of advanced brightness values according to the adjusted brightness value and the second brightness lower limit;

obtaining, by the processing unit, a plurality of advanced light source parameter sets each including one of the advanced brightness values;

controlling, by the processing unit, the light source to project light onto the article in a plurality of advanced projecting modes according to the advanced light source parameter sets, respectively;

capturing, by the image capturing device, a plurality of advanced images of the article when the article is lighted up by the light source in each of the advanced projecting modes;

obtaining, by the processing unit, a plurality of advanced image property data sets each being obtained from the advanced images that are captured in a respective one of the advanced projecting modes, and each including a plurality of property value sets that are related respectively to the image properties;

selecting, by the processing unit, an optimal image property data set from the advanced image property data sets according to the screening condition; and selecting, by the processing unit, an optimal light source parameter set that corresponds to the optimal image property data set from the advanced light source parameter sets.

10. The adaptive method of claim 9, wherein in the step of obtaining a second brightness lower limit, the second brightness lower limit is obtained by subtracting the second allowable brightness variation from the adjusted brightness value.

11. The adaptive method of claim 6, further comprising steps of:

analyzing, by the processing unit, the adjusted tonal value included in one of the adjusted light source parameter sets that is selected as the target light source parameter set to determine whether the adjusted tonal value is equal to the first tonal upper limit;

when the processing unit determines that the adjusted tonal value is equal to the first tonal upper limit, obtaining, by the processing unit, a second tonal upper limit based on the adjusted tonal value and a second allowable tonal variation;

obtaining, by the processing unit, a plurality of advanced tonal values according to the adjusted tonal value and the second tonal upper limit;

obtaining, by the processing unit, a plurality of advanced light source parameter sets each including one of the advanced tonal values;

controlling, by the processing unit, the light source to project light onto the article in a plurality of advanced projecting modes according to the advanced light source parameter sets, respectively;

capturing, by the image capturing device, a plurality of advanced images of the article when the article is lighted up by the light source in each of the advanced projecting modes;

obtaining, by the processing unit, a plurality of advanced image property data sets each being obtained from the advanced images that are captured in a respective one of the advanced projecting modes, and each including a plurality of property value sets that are related respectively to the image properties;

selecting, by the processing unit, an optimal image property data set from the advanced image property data sets according to the screening condition; and selecting, by the processing unit, an optimal light source parameter set that corresponds to the optimal image property data set from the advanced light source parameter sets.

12. The adaptive method of claim 11, wherein in the step of obtaining a second tonal upper limit, the second tonal upper limit is obtained by adding the second allowable brightness variation to the adjusted tonal value.

13. The adaptive method of claim 6, further comprising steps of:

analyzing, by the processing unit, the adjusted tonal value included in one of the adjusted light source parameter sets that is selected as the target light source parameter set to determine whether the adjusted tonal value is equal to the first tonal lower limit;

when the processing unit determines that the adjusted tonal value is equal to the first tonal lower limit, obtaining, by the processing unit, a second tonal lower limit based on the adjusted tonal value and a second allowable brightness variation;

obtaining, by the processing unit, a plurality of advanced tonal values according to the adjusted tonal value and the second tonal lower limit;

obtaining, by the processing unit, a plurality of advanced light source parameter sets each including one of the advanced tonal values;

controlling, by the processing unit, the light source to project light onto the article in a plurality of advanced projecting modes according to the advanced light source parameter sets, respectively;

capturing, by the image capturing device, a plurality of advanced images of the article when the article is lighted up by the light source in each of the advanced projecting modes;

obtaining, by the processing unit, a plurality of advanced image property data sets each being obtained from the advanced images that are captured in a respective one of the advanced projecting modes, and each including a plurality of property value sets that are related respectively to the image properties;

selecting, by the processing unit, an optimal image property data set from the advanced image property data sets according to the screening condition; and selecting, by the processing unit, an optimal light source parameter set that corresponds to the optimal image property data set from the advanced light source parameter sets.

14. The adaptive method of claim 13, wherein in the step of obtaining a second tonal lower limit, the second tonal lower limit is obtained by subtracting the second allowable brightness variation from the adjusted tonal value.

15. The adaptive method of claim 4, further comprising, before the step of selecting a candidate light source parameter, steps of:

controlling, by the processing unit, the light source to project light onto the article in the initial projecting modes one by one, according to the corresponding one of the initial light source parameter sets;

capturing, by the image capturing device, a plurality of initial images of the article when the article is lighted up by the light source in each of the initial projecting modes;

obtaining, by the processing unit, the initial image property data sets each being obtained from the initial images that are captured in the respective one of the initial projecting modes; and storing, by the processing unit, the initial image property data sets in the storage device.

16. The adaptive method of claim 4, wherein the step of selecting a candidate image property data set includes:

when the screening condition is related to only one of the image properties, for each of the initial image property data sets, calculating an initial score based on one of the property value sets of the initial image property data set according to $V_S = u_1 \times V + u_2 \times V \times \sigma$, where $V_S$ is the initial score, $u_1$ and $u_2$ are weights, $V$ is a first property value included in said one of the property value sets, and $\sigma$ is a second property value included in said one of the property value sets, said one of the property value sets being related to said one of the image properties to which the screening condition is related;

when the screening condition is related to multiple ones of the image properties and has a plurality of weights respectively for the multiple ones of the image properties, for each of the initial image property data sets, calculating the initial score based on multiple ones of the property value sets of the initial image property data set according to $$V_S = \sum_{n=1}^{N} W_n (u_1 \times V_n + u_2 \times V_n \times \sigma_n),$$

where N is a number of the multiple ones of the image properties, $W_n$ is a weight for an $n^{th}$ one of the multiple ones of the image properties, $V_n$ is the first property value included in an $n^{th}$ one of the multiple ones of the property value sets that is related to the $n^{th}$ one of the multiple ones of the image properties, and $\sigma_n$ is the second property value included in the $n^{th}$ one of the multiple ones of the property value sets, the multiple ones of the property value sets being related respectively to the multiple ones of the image properties to which the screening condition is related; and selecting one of the initial image property data sets that has the greatest initial score as the candidate image property data set.

* * * * *